US008379956B2

(12) United States Patent
Omernick et al.

(10) Patent No.: US 8,379,956 B2
(45) Date of Patent: Feb. 19, 2013

(54) SYSTEM AND METHOD FOR DEFINITION OF DICOM HEADER VALUES

(75) Inventors: Jon C. Omernick, Wauwatosa, WI (US); Tabb A. Patz, Milwaukee, WI (US); Tammy Michael Merisotis, Surfside Beach, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/231,320

(22) Filed: Sep. 13, 2011

(65) Prior Publication Data

US 2012/0002853 A1 Jan. 5, 2012

Related U.S. Application Data

(62) Division of application No. 11/281,635, filed on Nov. 17, 2005, now Pat. No. 8,041,093.

(60) Provisional application No. 60/673,971, filed on Apr. 22, 2005.

(51) Int. Cl.
*G06K 9/00* (2006.01)
*G06K 9/36* (2006.01)
*G06K 9/32* (2006.01)

(52) U.S. Cl. ........ 382/131; 382/128; 382/289; 382/296; 382/297

(58) Field of Classification Search .................. 382/128, 382/131
See application file for complete search history.

(56) References Cited

U.S. PATENT DOCUMENTS

| | | |
|---|---|---|
| 5,241,659 A | 8/1993 | Parulski et al. |
| 5,448,372 A | 9/1995 | Axman et al. |
| 5,779,634 A | 7/1998 | Ema et al. |
| 5,806,521 A | 9/1998 | Morimoto et al. |
| 5,864,331 A | 1/1999 | Anand et al. |
| 6,282,264 B1 | 8/2001 | Smith et al. |
| 6,851,851 B2 | 2/2005 | Smith et al. |
| 7,092,491 B2 | 8/2006 | Okoda |

(Continued)

FOREIGN PATENT DOCUMENTS

| | | |
|---|---|---|
| EP | 1224681 A1 | 7/2002 |
| EP | 1224681 A4 | 7/2003 |

(Continued)

OTHER PUBLICATIONS

"Content based image retrieval in medical applications for picture archiving and communication systems", Lehmann, Guld, Thies, Fischer, Keysers, Kohnen, Schubert, Wein, Proceedings of the SPIE Conference on Medical Imaging, vol. 5033, San Diego, CA, US, 2003.*

(Continued)

*Primary Examiner* — Michelle Entezari
(74) *Attorney, Agent, or Firm* — McAndrews, Held & Malloy, Ltd.; William Baxter

(57) ABSTRACT

Certain embodiments of the present invention provide an improved system and method for image file header configuration. Certain embodiments of the method include retrieving one or more criterion for configuration of an image orientation parameter, configuring the image orientation parameter based on the one or more criterion, obtaining image data, and storing the image data in an image file. The image file has a header portion including the image orientation parameter. In an embodiment, the image orientation parameter may be modified from a default configuration. The one or more criterion may include user preference, modality restriction, system preference, and/or rule, for example. The method may further include saving the image file with the configured image orientation parameter. Additionally, the method may include displaying an image according to the configured image orientation parameter. The image may be automatically oriented for display based on the configured image orientation parameter.

15 Claims, 5 Drawing Sheets

U.S. PATENT DOCUMENTS

| | | |
|---|---|---|
| 7,570,791 B2 | 8/2009 | Frank et al. |
| 8,098,981 B2 * | 1/2012 | Seo et al. ............... 396/50 |
| 8,134,571 B2 * | 3/2012 | Krishnan et al. ............ 345/581 |
| 2002/0071677 A1 | 6/2002 | Sumanaweera |
| 2002/0080921 A1 | 6/2002 | Smith et al. |
| 2004/0027359 A1 | 2/2004 | Aharon et al. |
| 2004/0081340 A1 | 4/2004 | Hashimoto |
| 2005/0030564 A1 * | 2/2005 | Su et al. ............... 358/1.9 |
| 2005/0063575 A1 | 3/2005 | Ma et al. |
| 2005/0165294 A1 | 7/2005 | Weiss |
| 2006/0047854 A1 * | 3/2006 | Oh et al. ............... 709/246 |
| 2006/0061599 A1 | 3/2006 | Yu et al. |
| 2006/0214097 A1 | 9/2006 | Wang et al. |
| 2007/0236517 A1 | 10/2007 | Kimpe |

FOREIGN PATENT DOCUMENTS

| | | | |
|---|---|---|---|
| EP | 1519557 | | 3/2005 |
| JP | 05056953 A | | 3/1993 |
| JP | 2002072386 A | | 3/2002 |
| JP | 2003527886 T | | 9/2003 |
| JP | 2004048817 A | * | 2/2004 |
| JP | 2005073706 A | | 3/2005 |
| WO | WO0126132 A1 | | 4/2001 |

OTHER PUBLICATIONS

"System integration and DICOM image creation for PET-MR Fusion", Hsiao, Fang, Wang, Guo, Chao, Yen, Journal of Digital Imaging, vol. 18, No. 1 (Mar.) 2005, p. 28-36.*

Office Action from the Japan Patent Office—Japanese Application No. 2006-114388, pp. 1-4, May 24, 2011.

* cited by examiner

FIG. 3

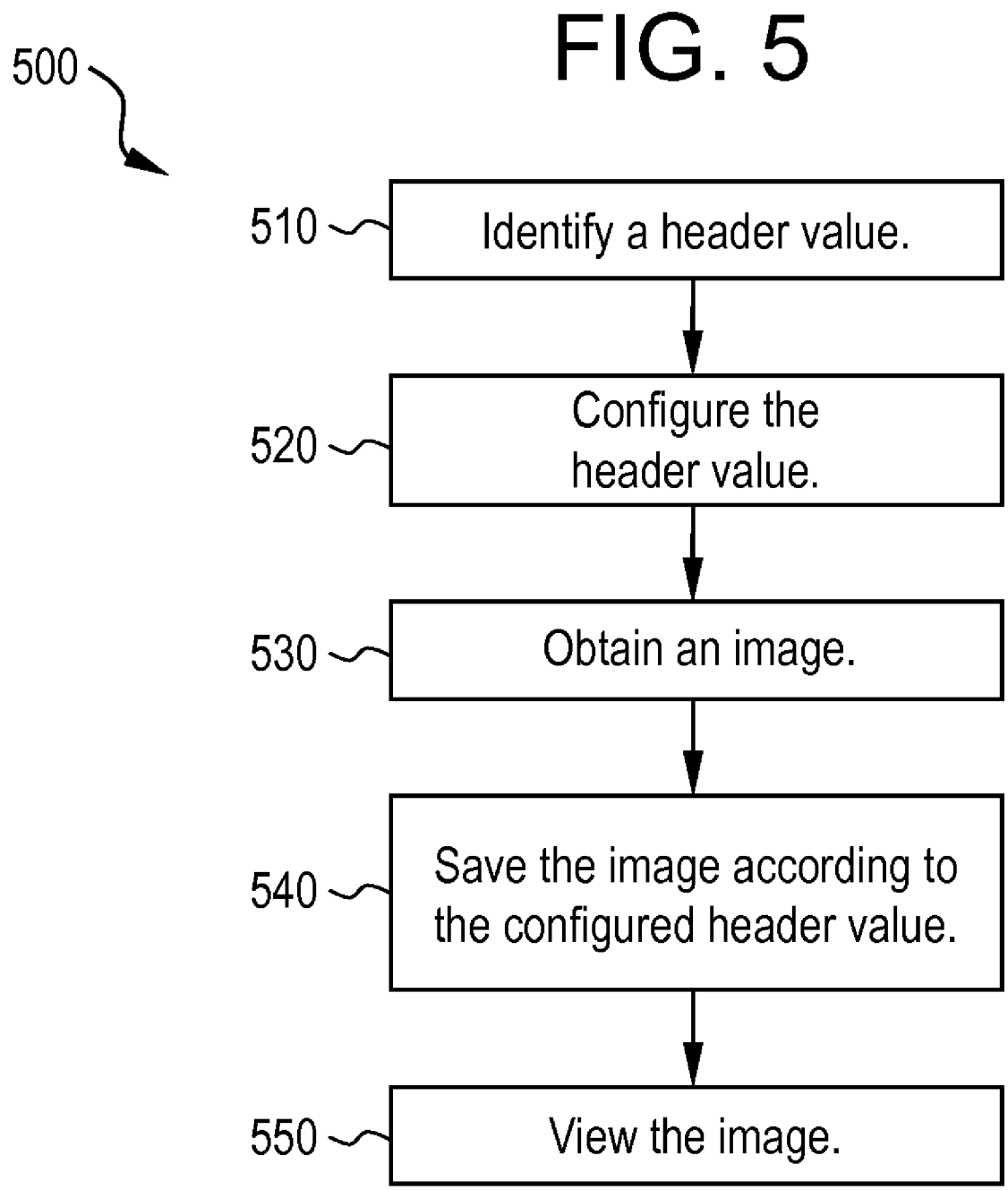

SYSTEM AND METHOD FOR DEFINITION OF DICOM HEADER VALUES

RELATED APPLICATIONS

The present application is a divisional and claims priority under 35 U.S.C. §121 to U.S. patent application Ser. No. 11/281,635, entitled "System and Method for Definition of DICOM Header Values," filed Nov. 17, 2005, now U.S. Pat. No. 8,041,093, which claims priority under 35 U.S.C. §119 (e) to U.S. Provisional Application Ser. No. 60/673,971 filed on Apr. 22, 2005, and entitled "System and Method for Definition of DICOM Header Values", the entire contents of each prior-filed application are hereby expressly incorporated by reference herein.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to image file header definition. In particular, the present invention relates to a system and method for defining parameters, such as image orientation, in an image file header.

Healthcare environments, such as hospitals or clinics, include clinical information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided among a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

Current medical information storage and management systems store and/or process large amounts of data. Additionally, medical data being processed and/or stored by medical information storage and management systems changes frequently. The large volume of data places a heavy burden on the systems processing and/or storing the data. Thus, a system and method for increased flexibility and improved processing of medical data would be highly desirable.

Many vendors in the medical imaging industry have established a communication standard to allow medical image data to be transmitted and processed by a plurality of disparate systems. One common standard is the Digital Imaging and Communications in Medicine (DICOM) protocol. DICOM is a standard for image and information transmission. DICOM relates to the transfer of electronic data, such as medical images and associated data, between medical diagnostic and imaging systems. The DICOM protocol may be employed in communication between medical devices and image archives, such as PACS.

The DICOM standard enumerates a command set, data formats, interface specifications, communication protocols, and command syntax. However, the DICOM standard does not specify details of implementation. DICOM sets forth Information Objects (types of data, such as computerized tomography, magnetic resonance, x-ray, ultrasound, etc.), Service Classes (actions with data, such as send, receive, print, etc.), and data transmission protocols. The Service Class User (SCU) protocol governs use of the DICOM service. The Service Class Provider (SCP) protocol governs the provider of the DICOM service. DICOM application services provide the ability to transfer images and image related data between DICOM applications. A DICOM service-object pair (SOP) is used to push and/or pull information between DICOM applications.

The DICOM protocol, such as the DICOM 3.0 protocol, is the standard digital communication protocol in radiology, cardiology and other medical imaging disciplines. The DICOM data model is organized in roughly three levels: a study level, a series level and an image level. For example, a series may be a group of images and a study may be a group of series. On a storage device, a study may include one or more image files. The image files include information related to the study and series of specific image(s).

A single DICOM file includes a preamble, a header and image data, for example. The preamble identifies the file as a DICOM file. The preamble is typically followed by characters "DICM" indicating that the file is a DICOM file. A DICOM header may include information such as patient name, scan type, image dimensions, file version, transfer syntax, etc. Information in the DICOM header may be organized into one or more groups, for example. DICOM image data may include two-dimensional or three-dimensional image data, for example. In an embodiment, DICOM image data may be compressed or encapsulated to reduce file size. DICOM image data may be compressed using image compression formats, such as JPEG or TIFF image compression, other compression scheme, for example.

A DICOM image file header may include information regarding image dimensions and may include additional information regarding the image data, for example. Image dimension information may include a number of frames, rows, and/or columns of image data, for example. Image dimension information may also include image resolution information, for example.

When images are sent from a digital radiology (Digital RAD) system, for example, a digital X-ray (DX) image type uses a number of parameters to be provided in the image header. Parameters included in the header are values that are designated in the DICOM standard as type 1, 2, or 3. Type 1 parameters are to be included in the header (patient name, etc.) and have a value. Type 2 parameters are included in the header, but the value may be blank. Type 3 parameters are optional to provide in the header (SID, Dose, etc.).

For a DX Image Object type, patient orientation (0020, 0020) is a type 1 DICOM parameter, for example. That is, the patient orientation parameter must be present in the header and must have a value associated with the parameter. The patient orientation parameter value designates an orientation of a patient as an image is viewed on a display from left to right and top to bottom. Typical values for the orientation parameter are AF (indicating patient anterior, patient foot), AP (indicating patient anterior, patient posterior) (as displayed on the monitor), etc. For fixed radiology systems, a user typically defines the patient orientation prior to X-ray exposures (similar process also used for MR, CT systems). Detector orientation in a fixed system is a constant, as the detector is typically fixed to a wall, floor, table, etc. For a portable detector, both the patient and the detector orientation may be changed, so requesting the user to set the orientation parameter prior to exposure is both prone to error and difficult to implement during a procedure involving mobile systems.

Thus, there is a need for a system and method for improved configuration of DICOM header parameters, such as image orientation.

BRIEF SUMMARY OF THE INVENTION

Certain embodiments of the present invention provide an improved system and method for image file header configuration. Certain embodiments of the method include identifying an image file header value to be configured, retrieving one or more criterion for configuration of the identified image file header value, and configuring the identified image file header value based on the one or more criterion. In an embodiment, the configuring step includes modifying the identified image file header value from a default configuration. The identified image file header value may include image orientation, for example. The one or more criterion may include user preference, modality restriction, system preference, and/or rule, for example. In an embodiment, the method further includes saving the configured image file header value. The method may also include displaying an image according to the configured image file header value. In an embodiment, the image may be automatically oriented for display based on the configured image file header value, for example.

Certain embodiments of a method for configuration of patient orientation information in an image file header include retrieving one or more criterion for configuration of an image orientation parameter, configuring the image orientation parameter based on the one or more criterion, obtaining image data, and storing the image data in an image file. The image file has a header portion including the image orientation parameter. In an embodiment, the configuring step further includes modifying the image orientation parameter from a default configuration. The one or more criterion may include user preference, modality restriction, system preference, and/or rule, for example. The image file may include a DICOM image file, for example. The method may further include saving the image file with the configured image orientation parameter. Additionally, the method may include displaying an image according to the configured image orientation parameter. In an embodiment, the method may automatically orient the image for display based on the configured image orientation parameter, for example.

Certain embodiments include a computer readable medium including a set of instructions for execution on a computer. The set of instructions includes an image file header analysis routine for analyzing information an image file header, and an image file header configuration routine for configuring at least one parameter of the image file header based on one or more criterion. The set of instructions may also include a user interface routine for inputting at least one of the one or more criterion for configuring the at least one parameter of the image file header. In an embodiment, the at least one parameter includes image orientation. The one or more criterion may include user preference, modality restriction, system preference, and/or rule, for example.

In an embodiment, the set of instructions further includes a display routine for displaying an image according to said image file header. In an embodiment, the image file header includes an image orientation parameter, and the display routine displays the image according to the image orientation parameter. The display routine may automatically orient the image for display based on the image orientation parameter, for example.

BRIEF DESCRIPTION OF SEVERAL VIEWS OF THE DRAWINGS

FIG. 3 illustrates a user interface and image acquisition in accordance with an embodiment of the present invention.

FIG. 5 illustrates a flow diagram for a method for definition of image file header values in accordance with an embodiment of the present invention.

Figure 1:
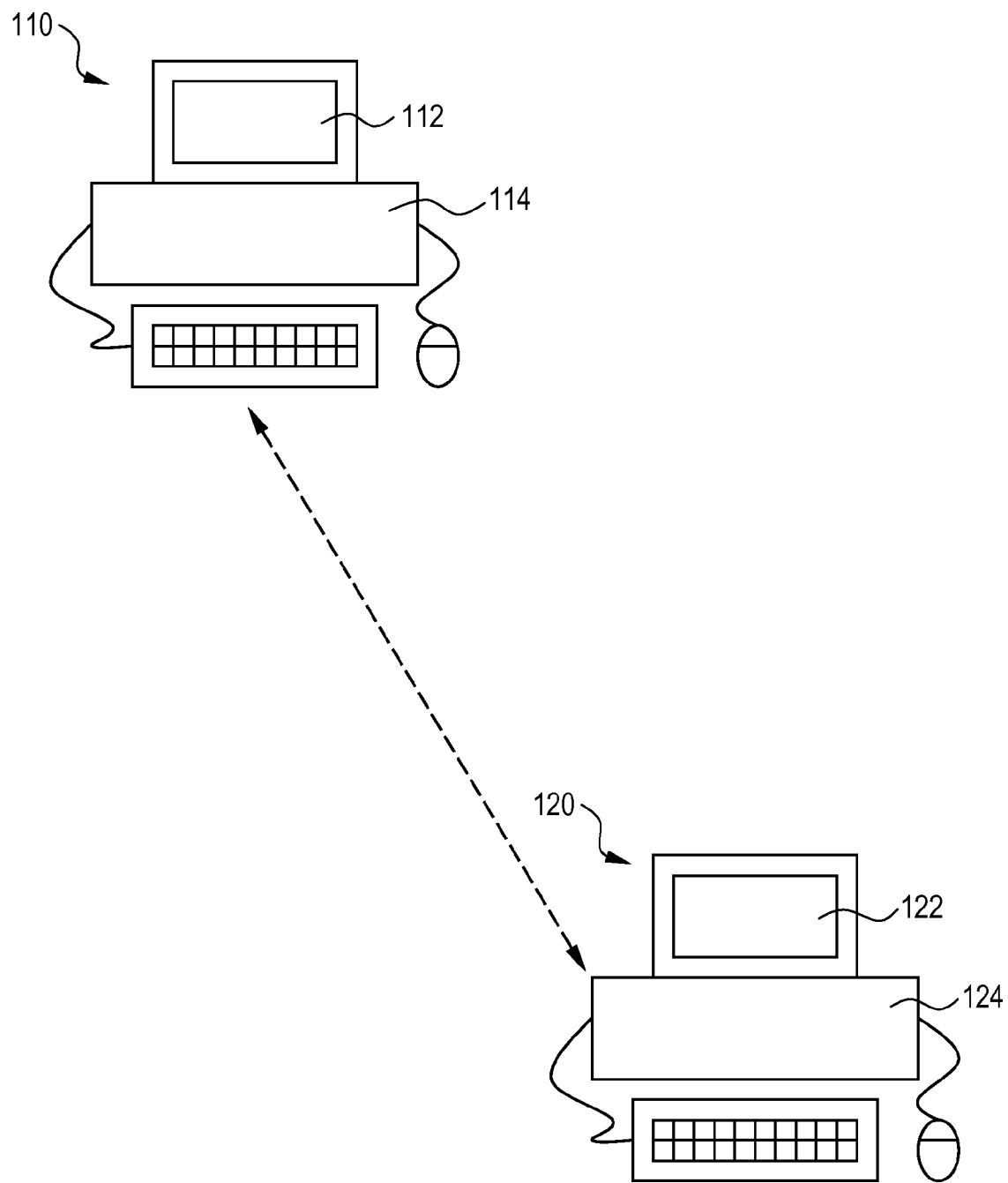
FIG. 1 illustrates an image management and communication system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates an image and information management system 100 used in accordance with an embodiment of the present invention. The image and information management system 100 includes a plurality of workstations 110, 120. The system 100 may be one or more of a plurality of medical information systems. In an embodiment, the image and information management system 100 may include a hospital information system (HIS), a radiology information system (RIS), a clinical information system (CIS), a cardiovascular information system (CVIS), a picture archiving and communication system (PACS), a library information system (LIS), an electronic medical record (EMR) system, and/or other image and information management system, for example.

The image and information management system 100 is capable of performing image management, image archiving, exam reading, exam workflow, and/or other medical enterprise workflow tasks, for example. The image management system 100 may include additional components such as an image manager for image management and workflow and/or an image archive for image storage and retrieval.

The image and information management system 100 may interact with one or more modalities, such as an x-ray system, computed tomography (CT) system, magnetic resonance (MR) system, ultrasound system, digital radiography (DR) system, digital X-ray (DX) system, positron emission tomography (PET) system, single photon emission computed tomography (SPECT) system, nuclear imaging system, and/or other modality. The image and information management system 100 may acquire image data and related data from the modality for processing and/or storage.

In an embodiment, the workstations 110, 120 include interfaces 112, 112 capable of allowing control of and exchange of information at the workstation 110, 120. The interface 112, 122 may be a graphical user interface (GUI) or other user interface that may be configured to allow a user to access functionality at the workstation 110, 120. The interface 112, 122 may be connected to an input device, such as a keyboard, mousing device, and/or other input device, for example.

Additionally, the workstations 110, 120 may include communication devices 114 and 124, respectively, to allow communication between the workstations 110, 120 and/or other external systems, for example. The communication devices 114, 124 may include a modem, wireless modem, cable modem, Bluetooth™ wireless device, infrared communication device, wired communication device, and/or other communication device, for example. The communication devices 114, 124 communicate and transfer data via one or more communication protocols, such as the DICOM protocol. The communication devices 114, 124 coordinate with processors in the workstations 110, 120 to establish a connection between the workstations 110, 120 and remotely execute functionality and/or transfer data, for example.

Figure 2:
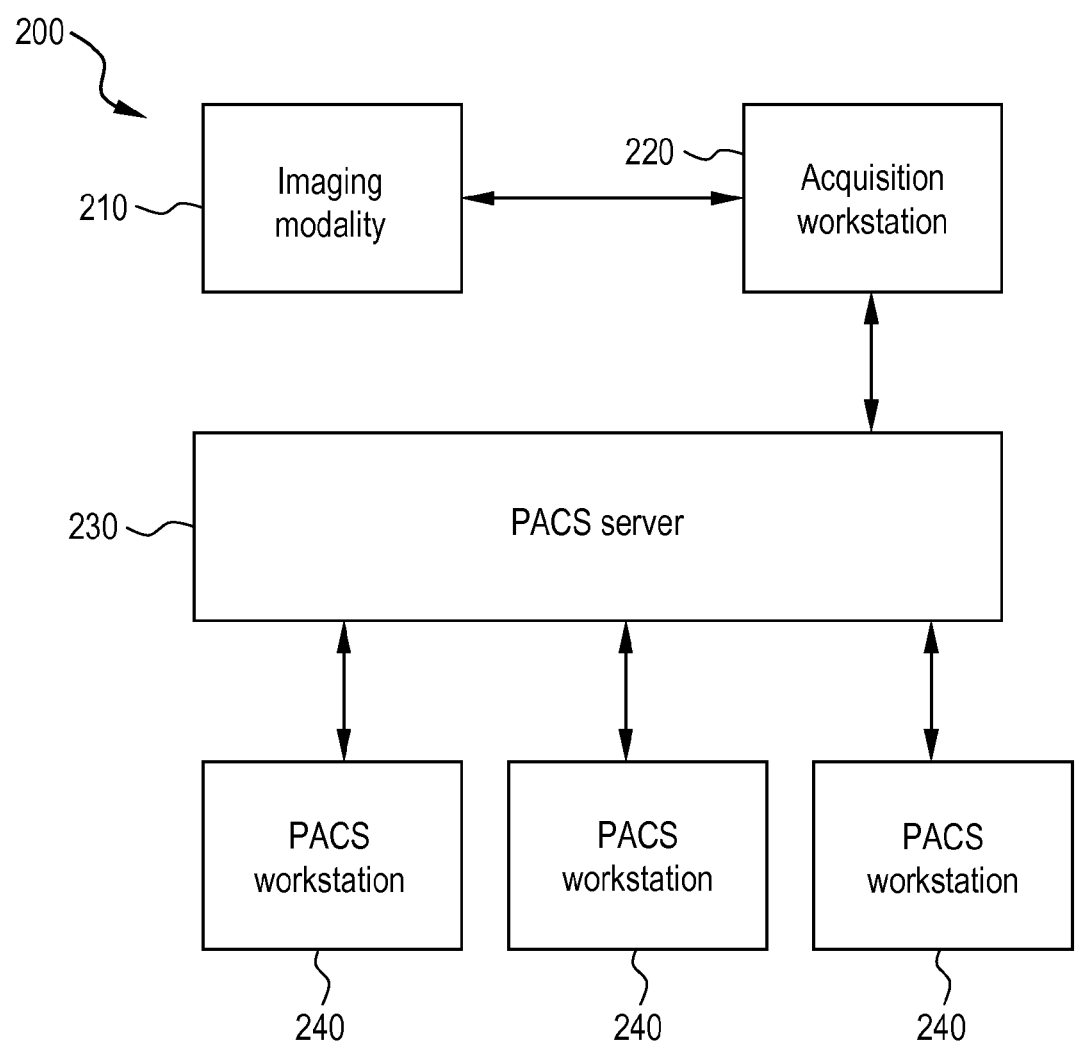
FIG. 2 illustrates an exemplary Picture Archiving and Communication System (PACS) system in accordance with an embodiment of the present invention.
Figure 4:
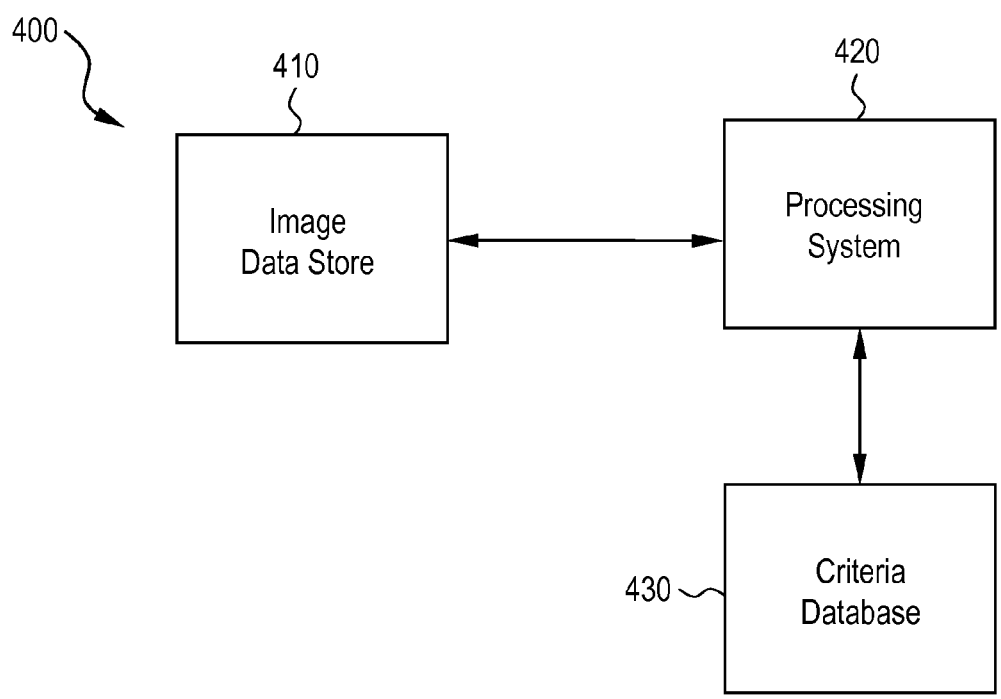
FIG. 4 illustrates an image header processing system used in accordance with an embodiment of the present invention.

FIG. 2 illustrates an exemplary Picture Archiving and Communication System (PACS) system 200 in accordance with an embodiment of the present invention. The PACS system 200 includes an imaging modality 210, an acquisition workstation 220, a network server 230, and one or more display workstations 240. The system 200 may include any number of imaging modalities 210, acquisition workstations 220, network servers 230 and display workstations 240 and is not in any way limited to the embodiment of system 200 illustrated in FIG. 2.

In operation, the imaging modality 210 obtains one or more images of a patient anatomy. The imaging modality 210 may include any device capable of capturing an image of a patient anatomy such as a medical diagnostic imaging device. For example, the imaging modality 210 may include an X-ray imager, ultrasound scanner, magnetic resonance imager, or the like. Image data representative of the image(s) is communicated between the imaging modality 210 and the acquisition workstation 220. The image data may be communicated electronically over a wired or wireless connection, for example.

In an embodiment, the acquisition workstation 220 may apply one or more preprocessing functions to the image data in order to prepare the image for viewing on a display workstation 240. For example, the acquisition workstation 220 may convert raw image data into a DICOM standard format or attach a DICOM header. Preprocessing functions may be characterized as modality-specific enhancements, for example (e.g., contrast or frequency compensation functions specific to a particular X-ray imaging device), applied at the beginning of an imaging and display workflow. The preprocessing functions may differ from processing functions applied to image data in that the processing functions are not modality specific and are instead applied at the end of the imaging and display workflow (for example, at a display workstation 240).

The image data may then be communicated between the acquisition workstation 220 and the network server 230. The image data may be communicated electronically over a wired or wireless connection, for example.

The network server 230 may include computer-readable storage media suitable for storing the image data for later retrieval and viewing at a display workstation 240. The network server 230 may also include one or more software applications for additional processing and/or preprocessing of the image data by one or more display workstations 240, for example.

One or more display workstations 240 are capable of or configured to communicate with the server 230. The display workstations 240 may include a general purpose processing circuit, a network server 230 interface, a software memory, and/or an image display monitor, for example. The network server 230 interface may be implemented as a network card connecting to a TCP/IP based network, but may also be implemented as a parallel port interface, for example.

The display workstations 240 may retrieve or receive image data from the server 230 for display to one or more users. For example, a display workstation 240 may retrieve or receive image data representative of a computed radiography (CR) image of a patient's chest. A radiologist may then examine the image for any objects of interest such as tumors, lesions, etc.

The display workstations 240 may also be capable of or configured to apply processing functions to image data. For example, a user may desire to apply processing functions to enhance features within an image representative of the image data. Processing functions may therefore adjust an image of a patient anatomy in order to ease a user's diagnosis of the image. Such processing functions may include any software-based application that may alter a visual appearance or representation of image data. For example, a processing function can include any one or more of flipping an image, zooming in an image, panning across an image, altering a window and/or level in a grayscale representation of the image data, and altering a contrast and/or brightness an image.

In an embodiment, the image and information management system 100 and/or PACS 200 stores, receives, transmits and/or generates image and associated data, such as DICOM data. DICOM image data files include header information defining the image file and the image data included in the image file. The file header includes orientation information, for example. In an embodiment, DICOM image file header information, such as image orientation information, may be preconfigured to minimize later interaction or manual manipulation by a user such as a radiologist.

Certain imaging systems, such as mobile imaging systems (e.g., mobile digital X-ray systems), introduce particular problems for users and image processing systems due to the variability of both detector position and patient/image position, for example. In an embodiment, a technician workflow includes positioning a detector and positioning a source, such as an X-ray tube, with respect to a patient. Then, an exposure is taken for each view in an imaging worklist. Next, a quality control inspection is performed with respect to the obtained image(s) to determine whether the image(s) satisfy an acceptable quality level. After quality control, the examination is closed, and image(s) are output, such as by printing and/or transmission of image data via network, electronic mail, and/or facsimile. With current mobile imaging systems, both detector orientation and patient or image orientation may be adjusted to store correct detector and image orientation information in an image file header, such as a DICOM file header. In certain embodiments, the image orientation value may be preconfigured in the image file header to reduce error, minimize manual interaction with the image file, and ensure that the Type 1 header parameter is filled, for example. Providing a correct header value to a technician or other user may help to avoid issues during examination setup and allows sites to clarify to the technician the desired orientation.

In an embodiment, patient orientation is based on an imaging protocol selected (for example, Head, Abdomen, etc.) and is displayed to a user but is not selectable. Patient orientation is based on application review and understanding of radiologist preference, for example. A site administrator may also modify the patient orientation parameter based on site specific desires or other rules, for example. In an embodiment, the patient orientation value may be adjusted for each imaging protocol. For example, some practitioners prefer "feet up" in an image, and some practitioners prefer a "feet down" orientation. A user interface may be provided to display a desired view and eliminate selection of image orientation by a user (e.g., by automatically using the "default" patient orientation value set in the system).

After an exposure is taken, the patient orientation value is used as the "implicit" orientation, and the user rotates or flips the image to match the patient orientation value. In an embodiment, the orientation header value does not change during image rotation since the image is being rotated to achieve the desired orientation. By maintaining an image orientation during rotation and processing of an image, a technician's workflow is streamlined because a radiologist does not have to rotate images sent to the PACS 200 prior to viewing by the radiologist, for example.

Figure 3:
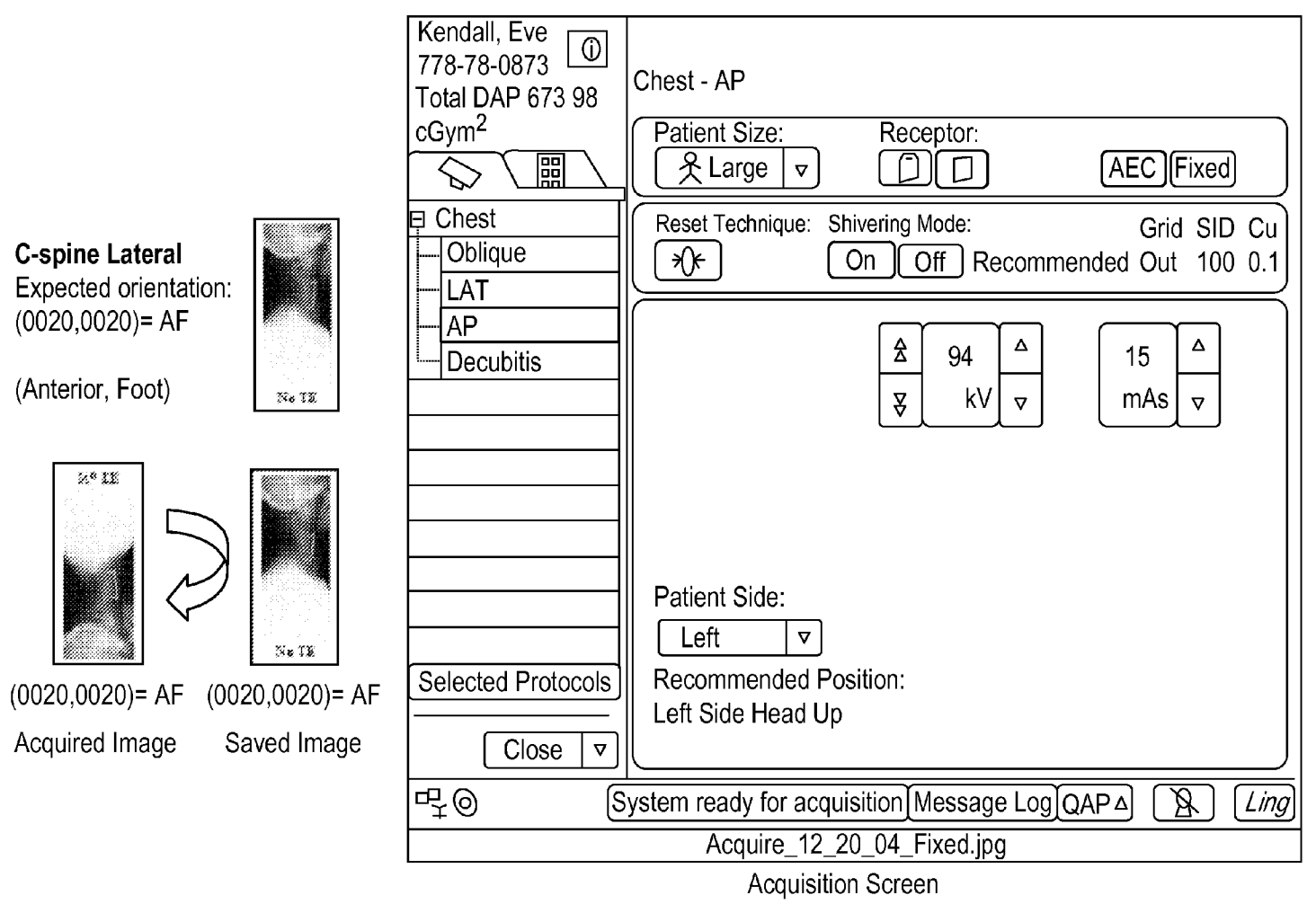

In an embodiment, a user interface is provided to allow a technician or other user to specify parameters or characteristics of image acquisition(s) (see, e.g., FIG. 3). In an embodiment, patient and/or image orientation may be preconfigured by an administrator, system software, and/or other parameters/rules, for example. A patient position may be suggested by the interface or other system to the user, for example. An image is acquired from a modality and rotated to match an expected image orientation. The rotated image is then saved with the desired orientation. A radiologist or other practitioner may then view the saved image with the expected orientation.

For example, as shown in FIG. 3, a lateral C-spine image may be obtained from a digital X-ray system. An image orientation, such as AF (Anterior, Foot), may be preconfigured based on radiologist preference or other information. The acquired C-spine image is adjusted to conform to an AF orientation according to the preconfigured image orientation information. Then, the adjusted image is saved with the AF orientation, such as in a PACS. When the image is later viewed, the image may be displayed according to the expected or preconfigured orientation without additional interaction from the radiologist or technician. Thus, an image orientation is incorporated into the imaging protocol. The radiologist or technician may know or assume an orientation of an image, based on the preconfigured or default orientation value, for example, without modifying or interacting with the image.

In an embodiment, an image header processing system 400 may be integrated with and/or used in conjunction with the image and information management system 100 and/or PACS 200 to analyze and configure image file header parameters. The system 400 may be implemented in software, firmware, and/or in hardware. The system 400 retrieves image files from an image data store 410, such as an imaging modality, image and information management system 100, and/or PACS 200. Image file(s) are transferred to the processing system 420. The processing system 420 analyzes header information from the image file(s). Using default value(s), user preference(s), system and/or modality parameter(s), and/or rule(s), for example, the processing system 420 configures one or more image file header parameters in the image file(s). In an embodiment, a criteria database 430 stores default value(s), user preference(s), system and/or modality parameter(s), rule(s), and/or other information used to configure header parameters. The database 430 may be a database, library, set of information, or other storage accessed by and/or incorporated with the processing system 420, for example. Thus, the processing system 420 may access the criteria database 430 to retrieve information, such as image orientation, to configure one or more image file header parameters in one or more image files. In an embodiment, the components of the system 400 may be implemented separately and/or integrated in various forms.

FIG. 5 illustrates a flow diagram for a method 500 for definition of image file header values used in accordance with an embodiment of the present invention. First, at step 510, a header value, such as a DICOM image file header value, is identified. For example, an image orientation header value is identified for a DICOM image file. Then, at step 520, the header value is configured based on certain criteria. For example, the image orientation header value is configured based on user preference, modality restrictions and/or system rules, etc.

Next, at step 530, an image is obtained from a modality. For example, an X-ray image is obtained. At step 540, the image is saved according to the configured header value(s). For example, the X-ray image is saved with an image orientation value in the image file header as previously configured based on user preference, modality restriction, and/or system rule(s). Then, at step 550, the image is viewed. For example, a radiologist may view the saved X-ray image. The image may be viewed according to the parameters found in the image file header. Thus, for example, the image may be viewed according to the image orientation information stored in the image file header.

Thus, certain embodiments connect a radiology technician workflow to orientation of images prior to sending the images to a PACS as part of a quality control (QC) check of the DICOM header. Certain embodiments allow configuration of DICOM header information for the DX image type with mobile RAD systems having variable detector and patient orientation. Certain embodiments provide correct or default header values and avoid orientation issues during exam setup. Certain embodiments allow a preferred orientation to be selected on a site and/or user specific value to allow sites and/user to clarify a desired orientation to a technician. Certain embodiments provide a broad implementation and address a portable detector implementation with DX Image type or other portable or fixed detector type.

Certain embodiments provide an improved system and method for configuring DICOM image file headers. Certain embodiments provide a robust implementation that meets both the requirements of the DICOM standard and the workflow of a hospital environment. Certain embodiments reduce user errors and incorrect header information present in many current implementations. Selection of orientation prior to exposure is often ignored or misunderstood due to limitations of current user interfaces.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:
1. A method for image file header configuration, said method comprising:
performing by at least one computer, at least:
identifying an image file header value to be configured, wherein said identified image file header value comprises image orientation;

retrieving one or more criterion for configuration of the identified image file header value comprising image orientation; and configuring said identified image file header value comprising image orientation based on said one or more criterion; and capturing, by an imaging modality, an image for association with said configured image file header value, said image being captured after said identified image file header value comprising image orientation is configured.

2. The method of claim 1, wherein said configuring step comprises modifying said identified image file header value from a default configuration.

3. The method of claim 1, wherein said one or more criterion comprises a user preference.

4. The method of claim 1, comprising saving said configured image file header value.

5. The method of claim 1, comprising displaying said image according to said configured image file header value.

6. A system for configuring an image file header, said system comprising:
at least one processing device configured to:
identify an image file header value to be configured, wherein said identified image file header value comprises image orientation;

retrieve one or more criterion for configuration of the identified image file header value comprising image orientation; and configure said identified image file header value comprising image orientation based on said one or more criterion; and an imaging modality configured to capture an image for association with said configured image file header value, said image being captured after said identified image file header value comprising image orientation is configured.

7. The system of claim 6, wherein said configuring said identified image file header value based on said one or more criterion comprises modifying said identified image file header value from a default configuration.

8. The system of claim 6, wherein said one or more criterion comprises a user preference.

9. The system of claim 6, comprising a memory device configured to store said configured image file header value.

10. The system of claim 6, comprising a display configured to display said image according to said configured image file header value.

11. A non-transitory computer-readable storage medium encoded with a set of instructions for execution on a computer, the set of instructions comprising:
an identification routine configured to identify an image file header value to be configured, wherein said identified image file header value comprises image orientation;

a retrieval routine configured to retrieve one or more criterion for configuration of the identified image file header value comprising image orientation;

a preconfiguration routine configured to configure said identified image file header value comprising image orientation based on said one or more criterion; and an image acquisition routine configured to capture an image for association with said configured image file header value, said image being captured after said identified image file header value comprising image orientation is configured.

12. The non-transitory computer-readable storage medium encoded with the set of instructions of claim 11, wherein said preconfiguration routine modifies said identified image file header value from a default configuration.

13. The non-transitory computer-readable storage medium encoded with the set of instructions of claim 11, wherein said one or more criterion comprises a user preference.

14. The non-transitory computer-readable storage medium encoded with the set of instructions of claim 11, comprising a storage routine configured to save said configured image file header value.

15. The non-transitory computer-readable storage medium encoded with the set of instructions of claim 11, comprising a display routine configured to display said image according to said configured image file header value.

* * * * *